United States Patent
Langley et al.

(10) Patent No.: US 6,969,370 B2
(45) Date of Patent: Nov. 29, 2005

(54) DRIVE MECHANISM FOR AN INJECTION DEVICE

(75) Inventors: Christopher Nigel Langley, Leamington Spa (GB); Shane Alistair Day, Warwick (GB); Robert Frederick Veasey, Leamington Spa (GB); Robert Woolston, Warwick (GB)

(73) Assignee: DCA Design International Limited, Warwick (GB)

( * ) Notice: Subject to any disclaimer, the term of this patent is extended or adjusted under 35 U.S.C. 154(b) by 0 days.

(21) Appl. No.: 10/433,647

(22) PCT Filed: Dec. 21, 2001

(86) PCT No.: PCT/GB01/05704

§ 371 (c)(1),
(2), (4) Date: Jun. 6, 2003

(87) PCT Pub. No.: WO02/051471

PCT Pub. Date: Jul. 4, 2002

(65) Prior Publication Data

US 2004/0049156 A1    Mar. 11, 2004

(30) Foreign Application Priority Data

Dec. 22, 2000  (GB) ................................. 0031466.6

(51) Int. Cl.[7] ........................................... A61M 37/00
(52) U.S. Cl. ....................................................... 604/131
(58) Field of Search ............................ 604/30–34, 48, 604/500, 503, 505–509, 65–68, 118–119, 604/131, 290, 151–155, 245–254, 207–211; 128/DIG. 12, 13; 417/18–25

(56) References Cited

U.S. PATENT DOCUMENTS

| 4,619,646 A | 10/1986 | Hernandez et al. |
| 4,749,109 A | 6/1988 | Kamen |
| 4,921,487 A | 5/1990 | Buffet et al. |
| 5,747,350 A | 5/1998 | Sattler |
| 5,820,602 A | 10/1998 | Kovelman et al. |
| 6,042,571 A | 3/2000 | Hjertman et al. |

FOREIGN PATENT DOCUMENTS

| EP | 0 514 816 A1 | 5/1992 |
| GB | 094 628 A | 10/1982 |
| WO | WO 97/36623 | * 10/1997 |

* cited by examiner

Primary Examiner—Nicholas D. Lucchesi
Assistant Examiner—Michael M. Thompson
(74) Attorney, Agent, or Firm—Oliff & Berridge, PLC

(57) ABSTRACT

A drive mechanism for an injection device is disclosed in which piston means are selectively driven to expel medicament from within a medicament cartridge. The drive mechanism comprises a drive means (270), first means (278) associated with the drive means, second gear means (274) being moveable between a first position in wich only movement along its longitudinal axis is permitted and a second position in which the second gear means (274) is free to rotate about the longitudinal axis, the piston means (280) being associated with the second gear means (274), a housing (276) within which the first gear means (278) and the second gear means (274) are constrained for movement, and biassing means (282) located between the housing (276) and a second gear means (274) to bias the second gear means (274) to the first position.

16 Claims, 3 Drawing Sheets

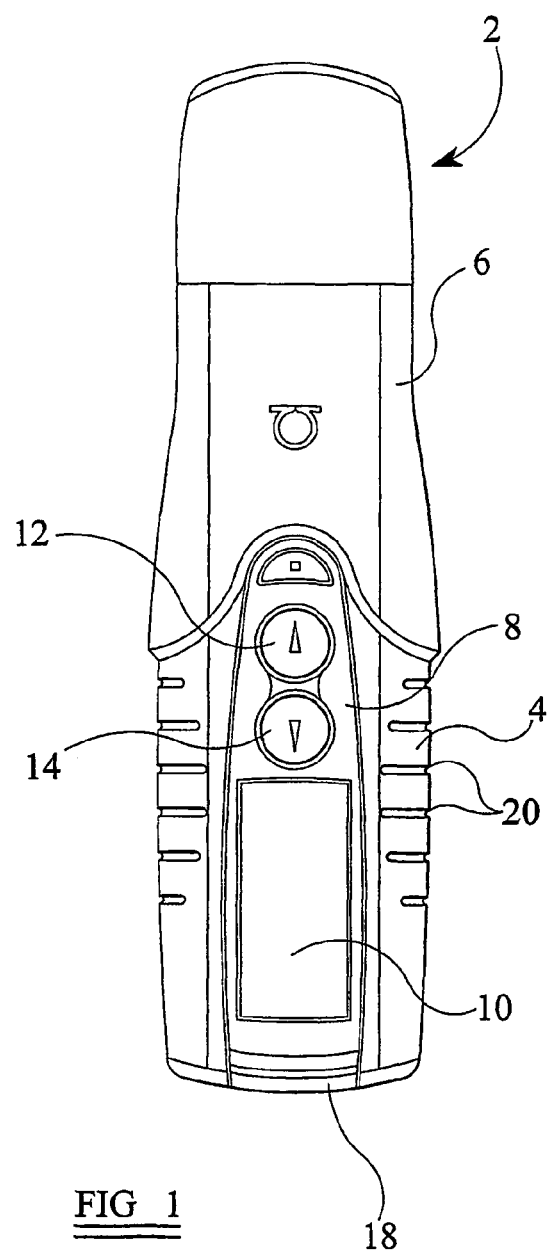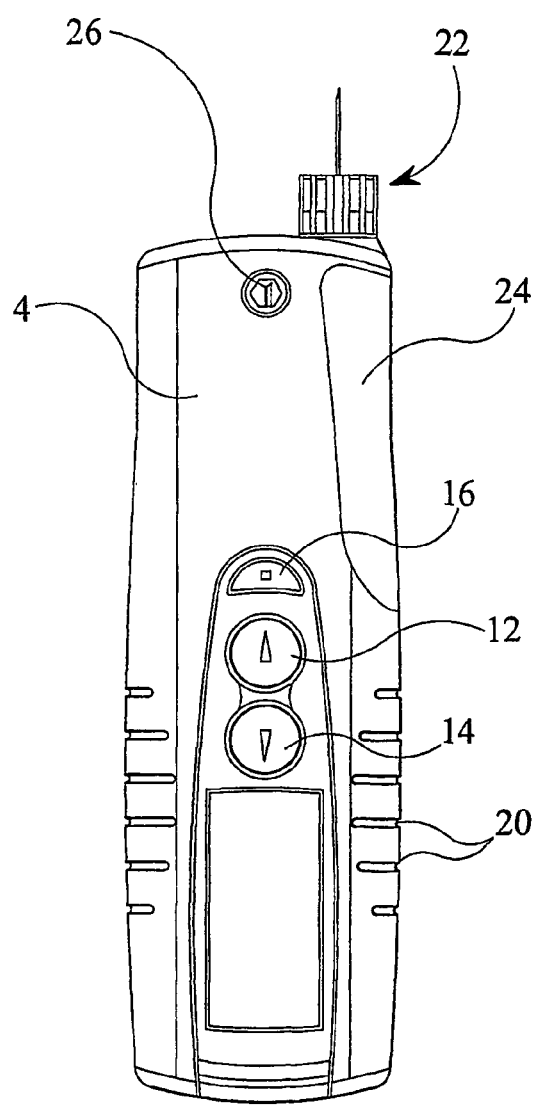
FIG 1
FIG 2

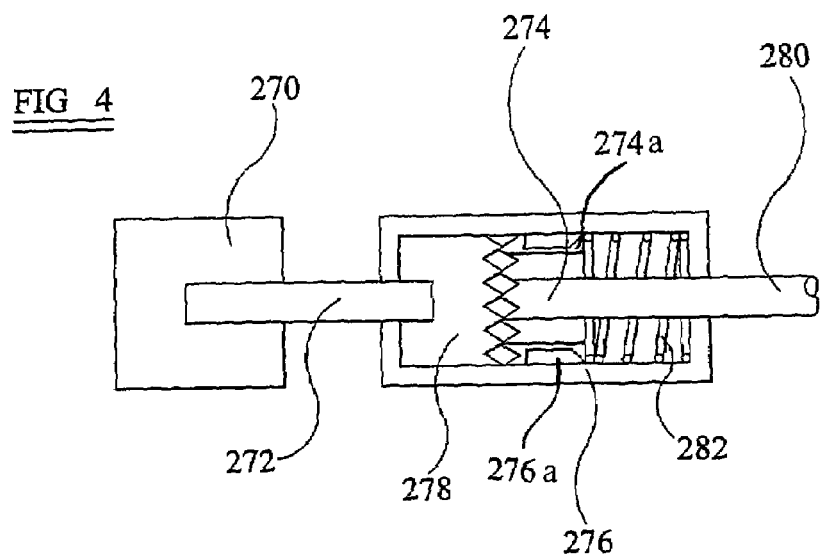
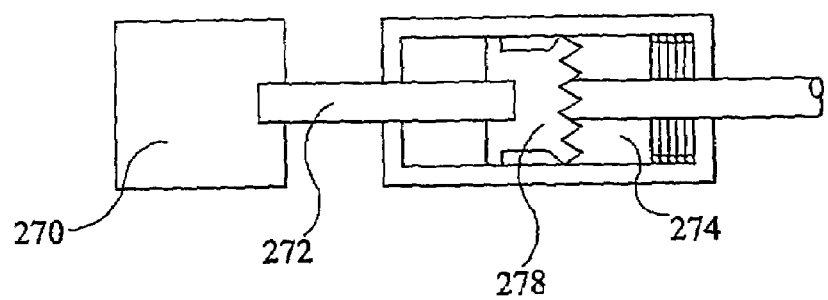
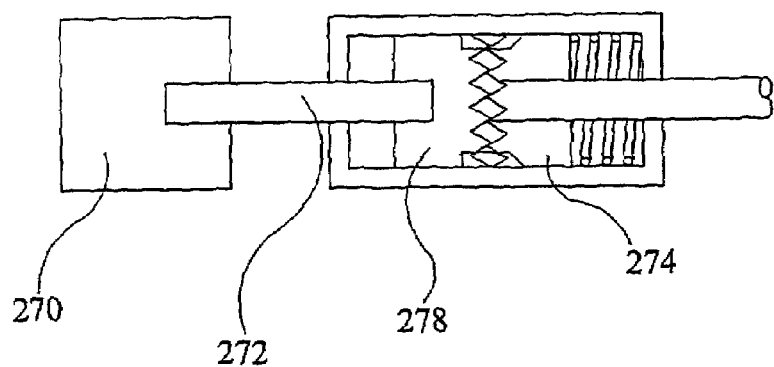

DRIVE MECHANISM FOR AN INJECTION DEVICE

The present invention relates to improvements in an injection device, and in particular to improvements in a portable injection device for dispensing controlled quantities of a medicament.

Typically such injection devices are used by those suffering from diabetes to administer a dose of insulin or insulin-type medicine to themselves. It will be understood that such injection devices are suitable for the injection of other medicines.

At one time, such doses were administered by use of a disposable syringe; the syringe first being filled from a separate phial or other container and then used to inject the dose. However, there were a number of difficulties in such an arrangement. In particular, such an arrangement was not suitable for the infirm. For others, the social stigma associated with such syringes made their public use problematic.

To overcome these difficulties a number of so-called pen-type injectors have been developed. These devices are small, being capable of being carried in a jacket pocket or the like and allow a number of doses to be obtained from a cartridge or ampoule contained within the injector. The present invention has particular application to such pen-type injectors.

While such pen-type injectors are a considerable improvement upon disposable hypodermic syringes, problems nevertheless remain.

In particular when considering the design of a drive system for a pen-type injector, there are a number of, sometimes, conflicting technical requirements. The drive system must be accurate and reliable, and at the same time compact and efficient. The drive system must be reliable and robust; being able to function for the life of the product. The drive system must also be intrinsically fail-safe.

It is an advantage of the present invention that it eliminates, or at least substantially reduces such problems. The present invention also provides for improved ease of use and improved interaction with a user.

The invention will now be described, by way of example only, with reference to the accompanying drawings; in which:—

FIG. 1 shows a plan view of a pen-type injector in accordance with the present invention;

FIG. 2 shows a similar view to FIG. 1 with an end cap of the injector omitted;

FIGS. 4 to 6 show in plan view a part of a still further drive mechanism through three stages of operation.

Figure 3:
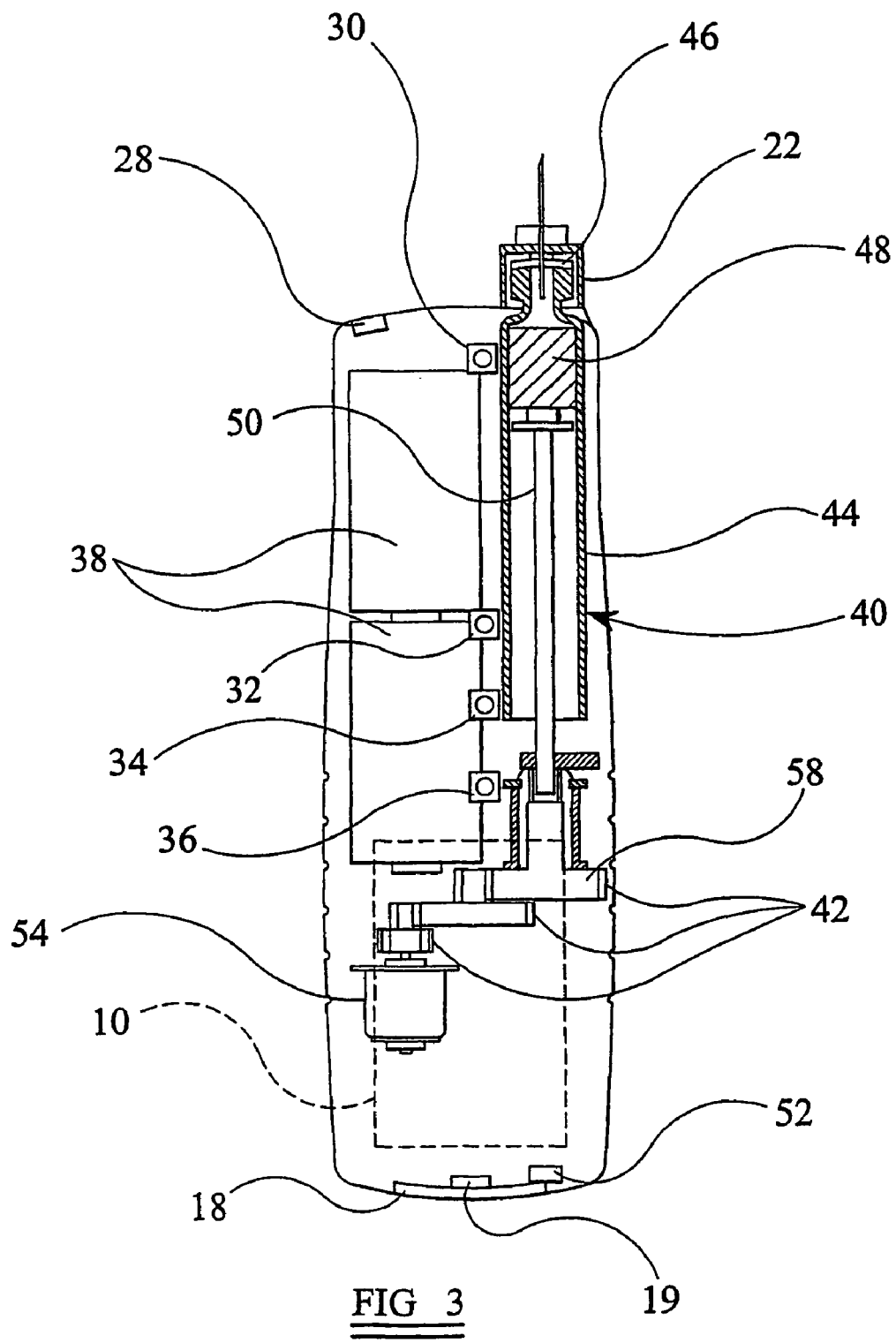
FIG. 3 shows a cross-sectional view of the injector of FIGS. 1 and 2.

Referring first to FIGS. 1 to 3, there can be seen a pen-type injector 2 in accordance with the present invention. The injector 2 comprises a main housing 4 to which is releasably secured an end cap or cover 6.

At a first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 10 in the illustrated embodiment also includes an arm button 16.

At the first end of the main housing there is also provided a dispense button 18. Preferably, when not depressed, the dispense button 18 is flush with the main housing 4.

Along a longitudinal axis of the injector 2, to each side of the control panel region 10 are provided a number of grooves or recesses 20. These aid in the gripping of the injector 2 by a user.

At a second end of the main housing 4 a needle unit 22 is releasably secured to the main housing. The second end of the main housing 4 is also provided with a shaped portion 24.

In use a cartridge 40 or ampoule of medicament is stored in the housing 4 behind the shaped portion 24. For preference, the shaped portion is transparent to permit the cartridge 40 to be seen by a user.

A primer button 26 is also provided on the second end of the housing 4. It will be understood that when the end cap 6 is in place over the second end of the housing, it will not be possible inadvertently to depress the primer button 26 or to be pricked by the needle unit 22. A cover detection switch 28 may also be included at the second end of the main housing 4 to detect whether the end cap or cover 6 is in place or not.

In FIG. 3, there can be seen a priming contact 30, an arm contact 32, a first dose contact 34 and a second dose contact 36 corresponding to the respective buttons. A dispense contact 19 corresponding to the dispense button 18 is also shown.

With reference to FIG. 3 it may be seen that there is provided a suitable location for a power source 38 such as a battery or batteries. There is also a suitable region in which a cartridge 40 or ampoule of medicament is to be located. This region may be accessed by way of the removable shaped portion 24 of the main housing 4 to allow for replacement of the cartridge 40 or ampoule as required by the user.

In a third region of the main housing 4 there is provided a drive mechanism 42 which operates from the power source 38 and acts upon the cartridge 40 or ampoule of medicament.

The cartridge 40 or ampoule comprises a container 44 or sleeve closed at one end by a cover 46 at a head end thereof, and sealed at the other by a movable bung 48 or stopper. When in position, the needle unit 22 pierces the cover 46 and movement of the bung 48 towards the cover 46 will cause the medicament contained within the cartridge 40 or ampoule to be expelled. The cartridge may be a 3 ml cartridge in accordance with ISO/FDIS 11608 Part 3, or any other suitable cartridge to suit the injector.

Movement of the bung 48 or stopper is caused by movement of a piston or plunger 50 forming a part of the drive mechanism 42. The piston or plunger 50 is movable between a first fully withdrawn position (not shown) which allows for the replacement of the cartridge 40 or ampoule and a second fully extended portion in which as much medicament as possible has been expelled from the cartridge 40 or ampoule. An end stop switch 52 may be provided in the main housing 4 to detect when the piston 50 is in the fully withdrawn position. Tripping of the switch end stop 52 may release a catch or other fastening device to allow access to the main housing 4 for replacement of the cartridge 40.

The drive mechanism 42 is operated by a motor 54 under the control of an electronic control unit (not shown). The motor 54 should be reversible in order to allow the piston 50 to be moved between the first and second positions. In FIG. 3, the motor 54 can be seen to drive the piston 50 by way of a gear train 42, such that rotation of a third rotor 58 causes the piston 50 to be moved in relation to the third rotor 58.

Preferably, the user can feel the vibration of the motor 54 and the associated drive mechanism 42 and/or hear them in operation. In this way an added degree of confidence in the fact of the operation of the injector 2 is provided to the user.

The functionality of a pen-type injector in accordance with the present invention will now be described, in particular with reference to FIGS. 1, 2 and 3.

The injector 2 is provided with an electronic control unit. The electronic control unit is coupled both to the drive mechanism and a user interface. The user interface includes the display panel 10 as well as the user operable buttons (and associated contacts). The electronic control unit is microprocessor based. Either volatile or non-volatile memory may be used for storage of 'dose history' and patient specific information.

The electronic control unit is preferably powered from the injector power source 38.

The injector 2 preferably also includes a port for communication between the electronic control unit and an external apparatus such as a personal computer.

The injector 2 also has a priming detection facility, (such as a tilt switch or accelerometer) to identify when the injector 2 is inverted. On detection of an inverted position (needle up) the injector 2 will automatically change state to be ready for priming. Priming may be initiated by depression of the primer button 26 to cause a fixed small dispense action. The electronic control unit may cause a speaker to sound when the primer button 26 is depressed.

The primer button 26 is inactive at all other times. When the primer button 26 is active, all other buttons in the control panel region are inactive, that is those buttons which are to be used to set or dispense a dose.

The electronic control unit may cause a speaker to sound when the arm button 16 is depressed for a sufficient period of time to provide audible feedback for the user.

The function of the arm button 16 is to make the dispense button 18 active. The arm button is preferably held down for a predetermined period of time before the injector 2 becomes armed. The armed status may additionally be shown on the display panel 10. The functionality of the arm button is preferably linked to the cover detection switch 28 such that the arm button 16 will only function to arm the injector 2 when the cover 6 is not present.

Additionally, in a preferred embodiment, a clock within the electronic control unit will detect whether the dispense button 18 has been pressed within a specified time interval following arming of the injector 2. If the dispense button 18 has not been depressed within the specified time interval the electronic control unit will disarm the injector 2. Alternatively, if the arm button is depressed a second time within a predetermined time period by the user, the injector will be disabled.

In an alternative embodiment, the dispense button 18 may function as both a prime button and the dose button. When the priming detector is actuated, by the injector 2 being oriented needle up, the dispense button 18 would change function to that of the prime button of the previous embodiment.

The buttons of the injector 2 are preferably tactile in nature to provide sensory feedback to the user.

The display panel 10 is typically an LCD display and will provide alphanumeric and graphical information relating to the operation of the device.

Due to the use of an electromechanical drive, the dispense action is initiated by the user operating a switch. This means that the force required to operate the dispense button can be optimised for the comfort and ergonomic requirement of users.

In FIGS. 4, 5 and 6, there is shown a drive mechanism in the form of a single indexing gear arrangement. A push pull solenoid 270 is shown having an output shaft 272. The output shaft is coupled to a driving gear 278. The driving gear 278 is driven longitudinally within a gear housing 276. A shaft 280 of a lead screw is coupled to a driven gear 274. The lead screw will be understood to comprise piston means for the advancement of bung 48 within a medicament cartridge 40 within the context of this description. The driven gear is located for movement longitudinally within the gear housing 276. Spring biassing means, typically a helical spring 282, are located between a rear face of the driven gear 274 and the gear housing 276 to urge the driven gear 274 toward the driving gear 278. Each of the driven gear 274 and the driving gear 278 are provided with angularly disposed teeth such that the teeth of the driven gear 274 may mate with the teeth of the driving gear 278.

The rotation of the driven gear 274 is aided by the presence of keyways 274*a* on the outer diameter of the driven gear 274 which engage with a set of splines 276*a* provided on an internal face of the housing 276. The splines 276*a* prevent the driven gear 274 from meshing completely with the driving gear 278. As the driving gear 278 advances on a push stroke of the solenoid 270, the driven gear 274 is pushed, against the spring biassing means 282, along the splines 276*a* until a point is reached where the driven gear 274 may disengage from the splines 276*a*. At this point, the driven gear 274 rotates under the combined action of the pushing force of the spring biasing means 282 and that of the solenoid 270 until the teeth of the driven gear 274 and the driving gear 278 mesh.

On a return stroke, the driven gear 274 is returned, under the action of the spring biassing means 282. However, due to the rotation the keyways now pick up the next spline location allowing the driven gear 274 to return to a longitudinal position corresponding to a start position, but angularly offset from the previous start position.

This drive mechanism has a number of advantages. In particular, it has no indeterminate position which night lead to jamming of the drive mechanism. Also, the drive mechanism latches at the end of each stroke, making accidental dispense unlikely.

What is claimed is:

1. A drive mechanism for an injection device in which piston means are selectively driven to expel medicament from within a medicament cartridge, the drive mechanism comprising:
   a drive means;
   a first gear means associated with the drive means;
   a second gear means moveable between a first position in which only movement along a longitudinal axis of the second gear means is permitted and a second position in which the second gear means is free to rotate about the longitudinal axis;
   a piston means associated with the second gear means;
   a housing within which the first gear means and the second gear means are constrained for movement; and
   a biasing means located between the housing and the second gear means to bias the second gear means to the first position.

2. A drive mechanism according to claim 1, wherein one of the second gear means and the housing is provided with a plurality of splines and the other of the second gear means and the housing is provided with keyways within which the splines are located when the second gear means is in the first position.

3. A drive mechanism according to claim 1, wherein a first movement of the drive means causes the first gear means to advance from an initial position towards the second gear means causing the second gear means to be displaced from the first position to the second position and a second movement of the drive means causes the first gear means to return to the initial position thereby allowing the second drive means to rotate and return to the first position under the action of the biasing means.

4. A drive mechanism according to claim 1, wherein the drive means comprised a push pull solenoid.

5. A drive mechanism according to claim 1, wherein the biasing means comprised a helical spring.

6. A drive mechanism according to claim 1, wherein the piston means comprises a lead screw.

7. A drive mechanism according to claim 2, wherein a first movement of the drive means causes the first gear means to advance from an initial position towards the second gear means causing the second gear means to be displaced from the first position to the second position and a second movement of the drive means causes the first gear means to return to the initial position thereby allowing the second drive means to rotate and return to the first position under the action of the biasing means.

8. A drive mechanism according to claim 2, wherein the drive means comprised a push pull solenoid.

9. A drive mechanism according to claim 3, wherein the drive means comprised a push pull solenoid.

10. A drive mechanism according to claim 2, wherein the biasing means comprised a helical spring.

11. A drive mechanism according to claim 3, wherein the biasing means comprised a helical spring.

12. A drive mechanism according to claim 4, wherein the biasing means comprised a helical spring.

13. A drive mechanism according to claim 2, wherein the piston means comprises a lead screw.

14. A drive mechanism according to claim 3, wherein the piston means comprises a lead screw.

15. A drive mechanism according to claim 4, wherein the piston means comprises a lead screw.

16. A drive mechanism according to claim 5, wherein the piston means comprises a lead screw.

* * * * *